United States Patent [19]
Ouchi

[11] Patent Number: 6,162,207
[45] Date of Patent: Dec. 19, 2000

[54] OPERATING UNIT FOR ENDOSCOPIC TREATMENT TOOL

[75] Inventor: Teruo Ouchi, Saitama, Japan

[73] Assignee: Asahi Kogaku Kogyo Kabushiki Kaisha, Tokyo, Japan

[21] Appl. No.: 09/135,839

[22] Filed: Aug. 18, 1998

[30] Foreign Application Priority Data

Aug. 18, 1997 [JP] Japan ..................................... 9-221281
Sep. 30, 1997 [JP] Japan ..................................... 9-283056
Sep. 30, 1997 [JP] Japan ..................................... 9-283057

[51] Int. Cl.[7] ................................................. A61B 17/00
[52] U.S. Cl. .................................................................... 606/1
[58] Field of Search ..................................... 600/104, 106, 600/562, 564; 606/1, 108, 110, 113

[56] References Cited

U.S. PATENT DOCUMENTS

| | | |
|---|---|---|
| 4,178,810 | 12/1979 | Takahashi . |
| 4,467,802 | 8/1984 | Maslanka .................................. 606/206 |
| 5,084,054 | 1/1992 | Bencini et al. .......................... 606/113 |
| 5,163,942 | 11/1992 | Rydell ...................................... 606/113 |
| 5,275,614 | 1/1994 | Haber et al. ............................. 606/207 |
| 5,376,094 | 12/1994 | Kline ........................................ 606/113 |
| 5,478,350 | 12/1995 | Kratsch et al. .......................... 606/205 |
| 5,489,288 | 2/1996 | Buelna ..................................... 606/144 |
| 5,542,948 | 8/1996 | Weaver et al. ........................... 606/113 |
| 5,562,619 | 10/1996 | Mirarchi et al. ........................... 604/95 |
| 5,667,476 | 9/1997 | Frassica et al. ......................... 600/149 |

Primary Examiner—John P. Leubecker
Attorney, Agent, or Firm—Greenblum & Bernstein P.L.C.

[57] ABSTRACT

An operating unit for an endoscopic treatment tool, which facilitates smooth operation of a medical or surgical treatment mechanism protruded from an end of an endoscope. A motion converting mechanism is provided inside the operating unit. The mechanism includes a pinion rotatably supported on a connecting rod of a finger-retaining portion, a first rack formed on a cylindrical body of the operating unit, and a second rack formed on a coupling member connected to the end of the connecting wire. The pinion meshes with both the first and second racks, so that the movement of the finger-retaining portion results in movement of the connecting wire, with a certain magnification.

15 Claims, 15 Drawing Sheets

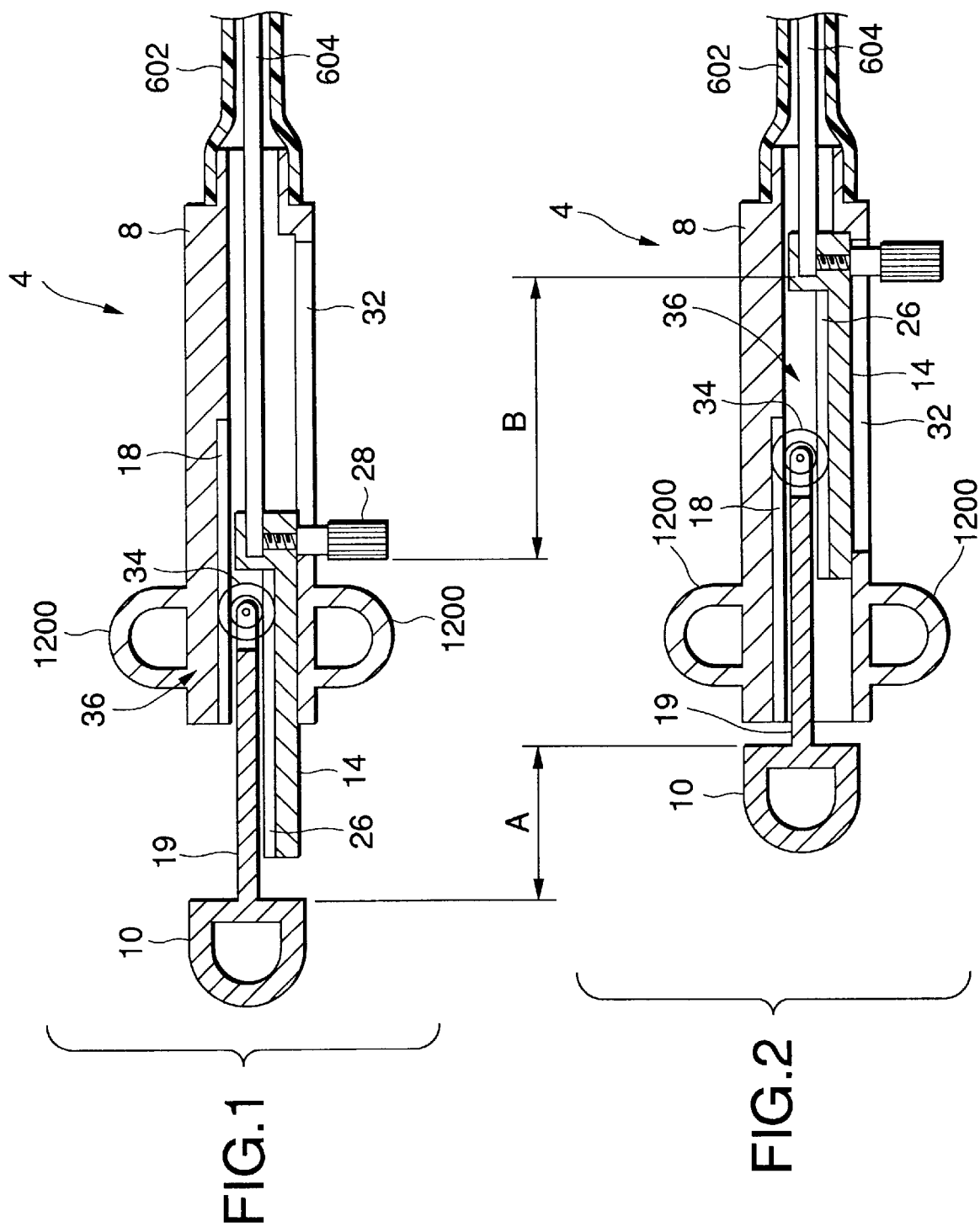

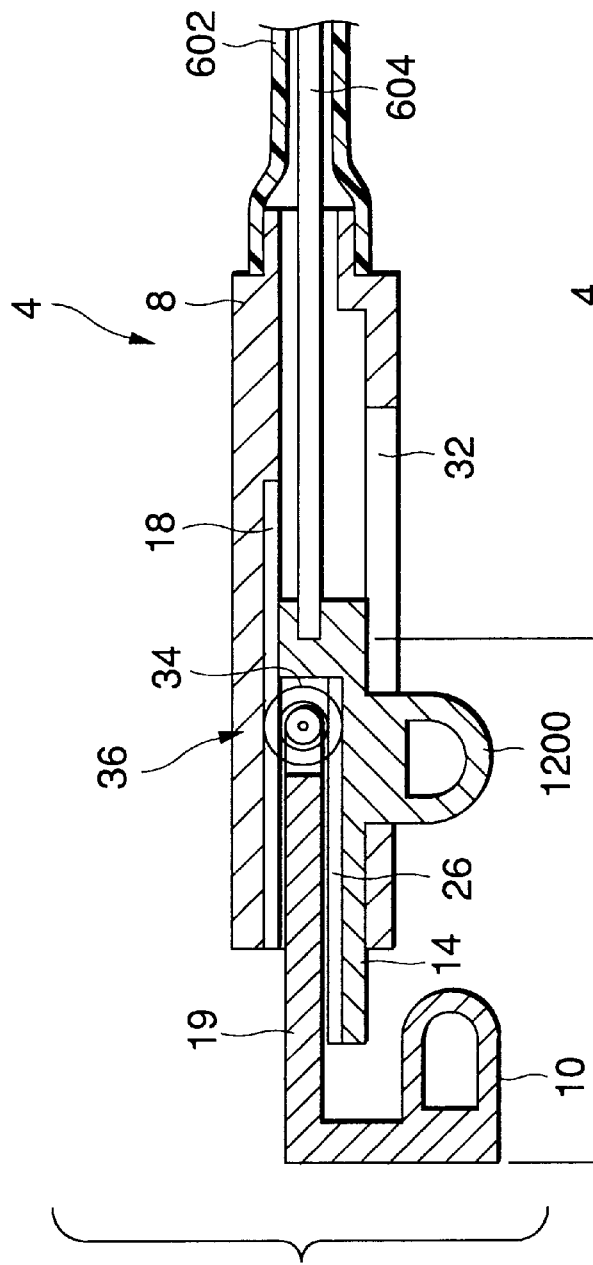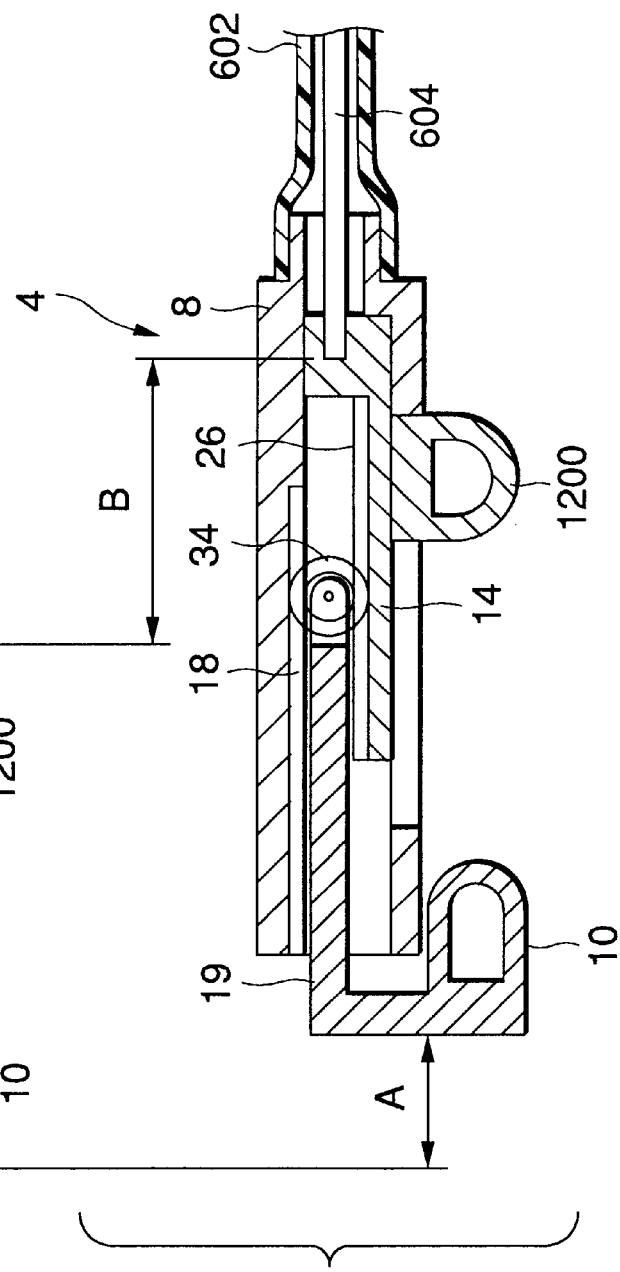

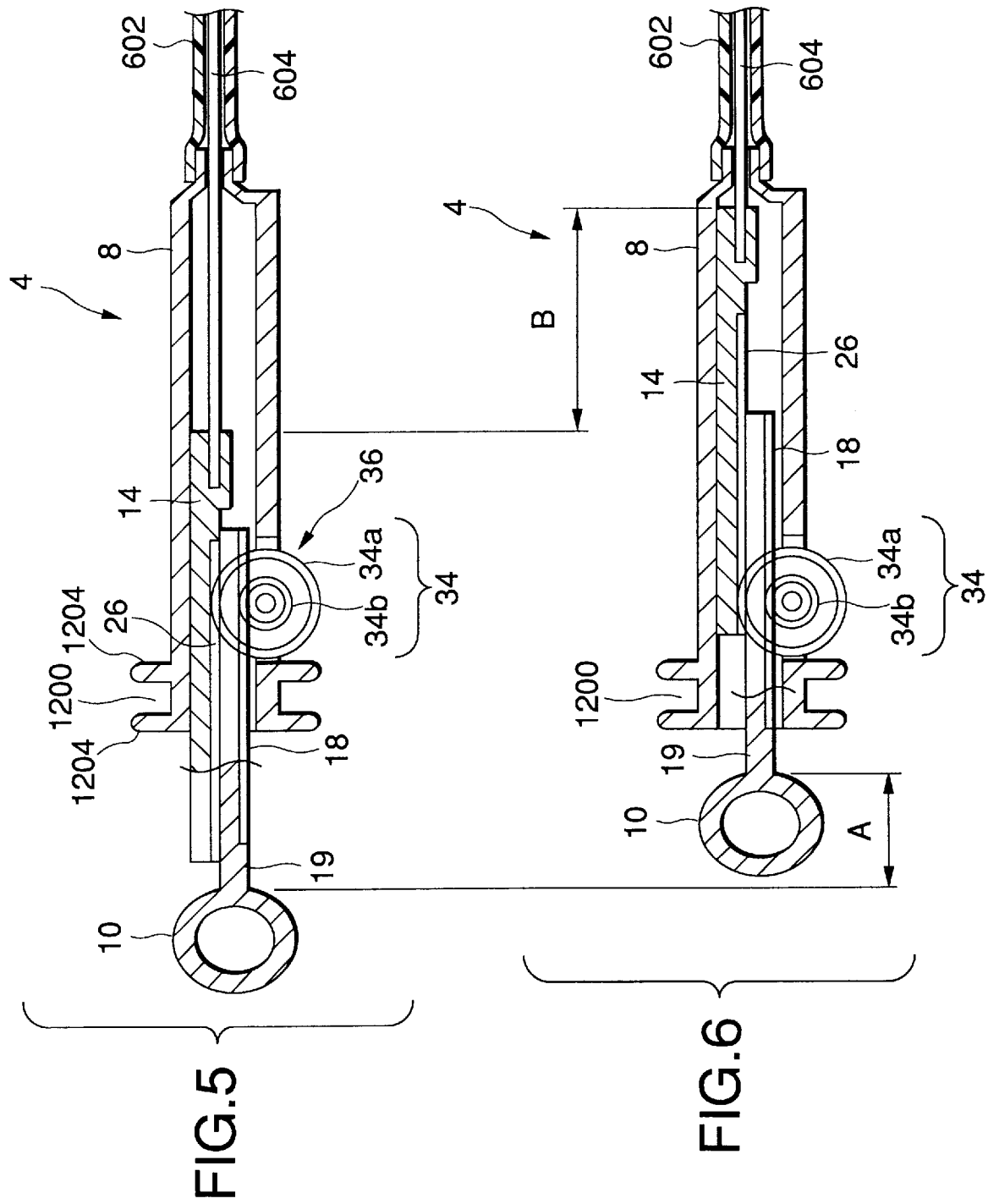

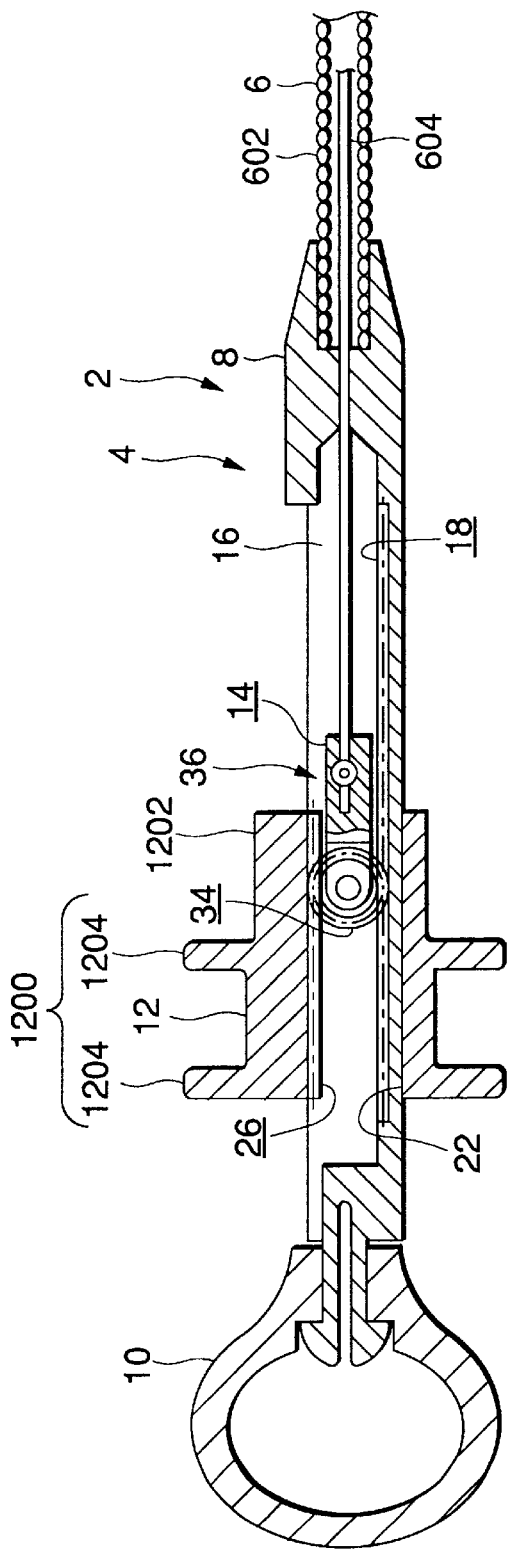
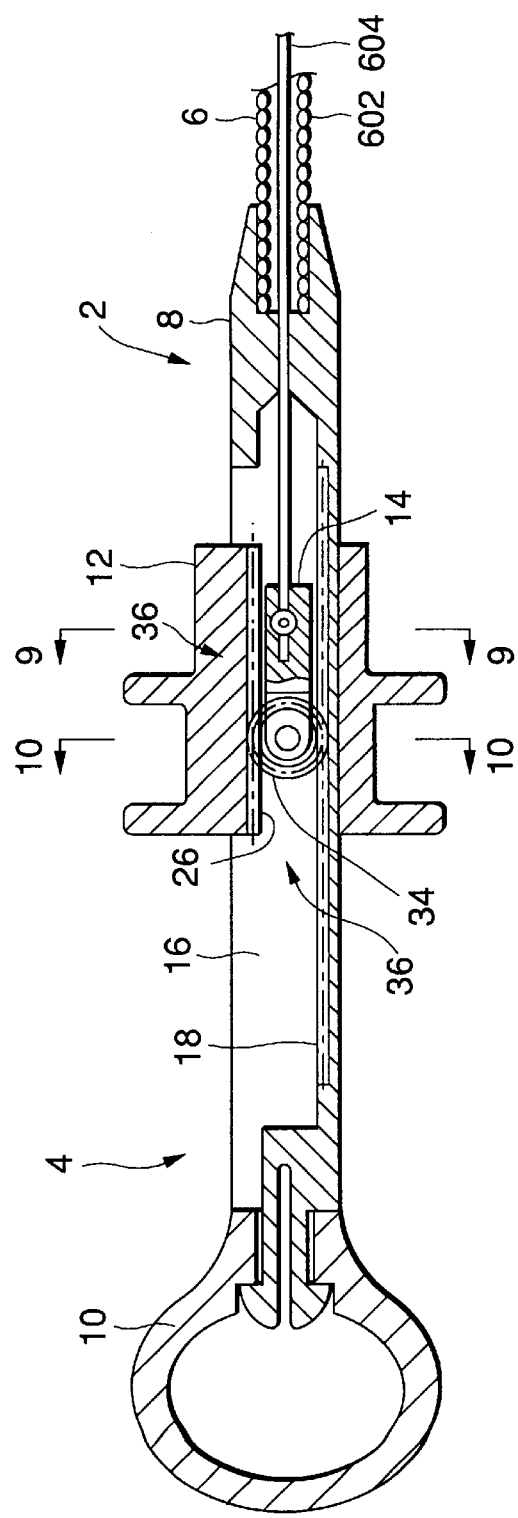
FIG. 8A
FIG. 8B

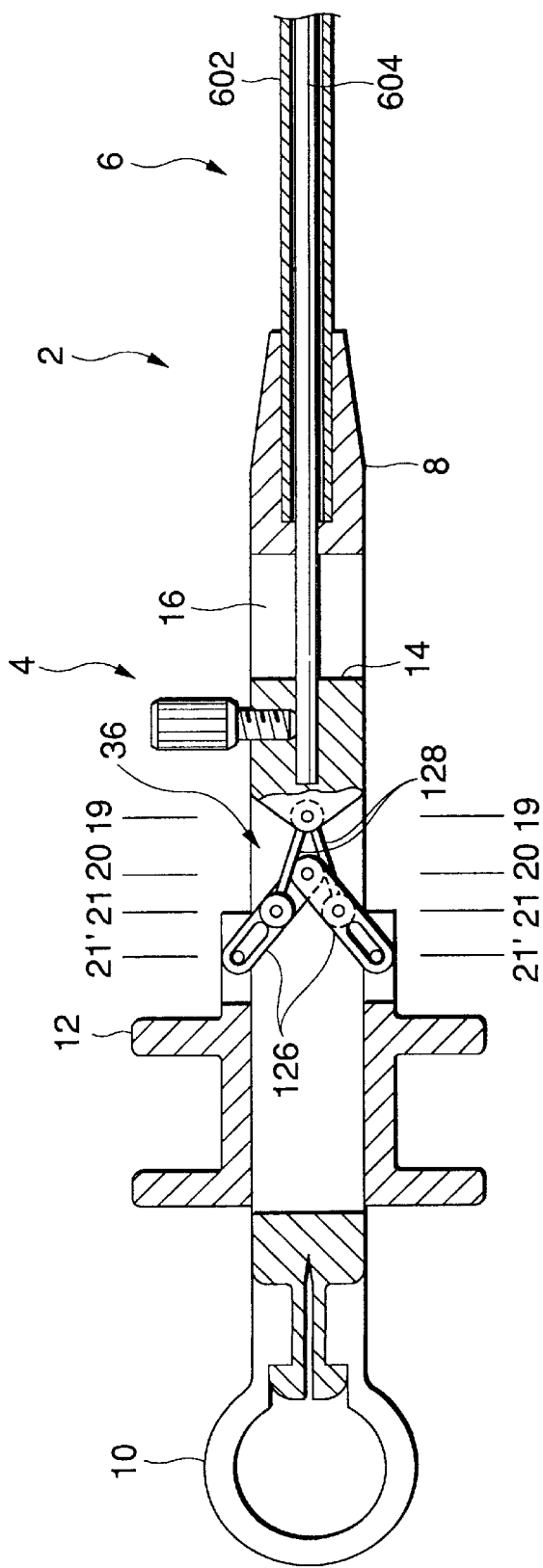

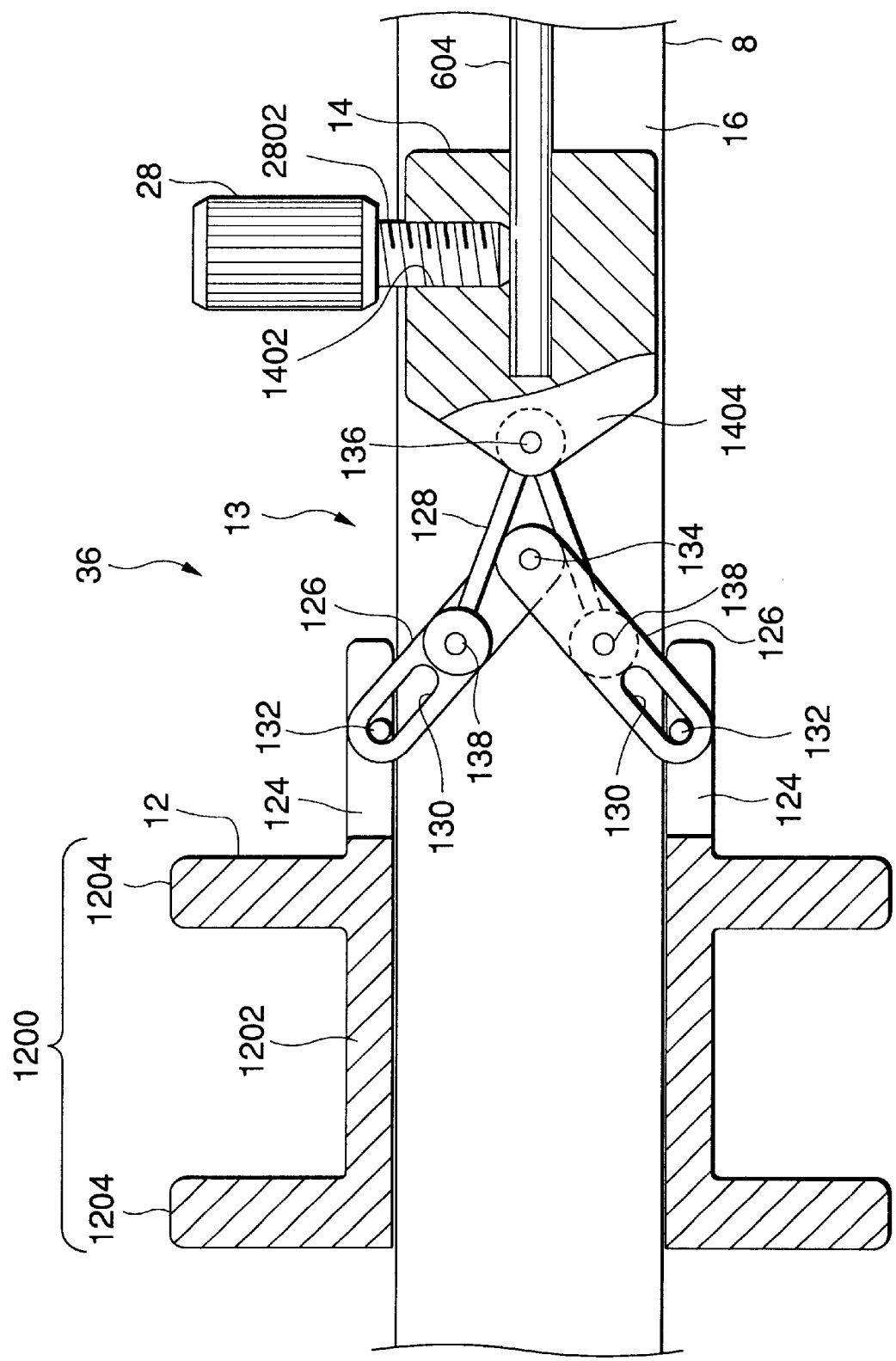

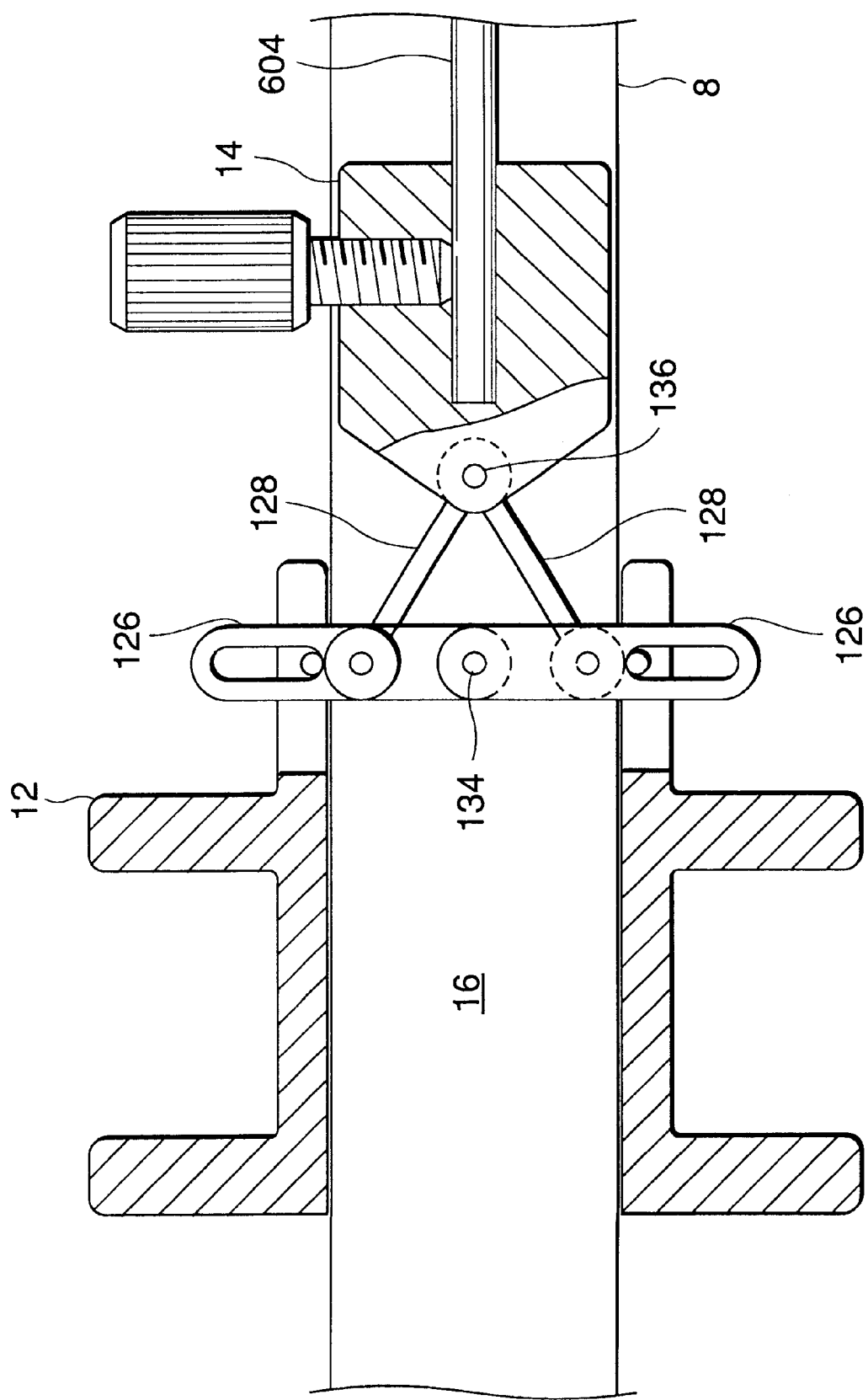

OPERATING UNIT FOR ENDOSCOPIC TREATMENT TOOL

BACKGROUND OF THE INVENTION

1. Field of the Invention

The present invention relates to an operating unit for an endoscopic treatment tool.

2. Description of the Prior Art

An endoscopic treatment tool generally includes a treatment mechanism for applying medical or surgical treatment to a human body, an operating unit distanced from the treatment mechanism, and a connecting wire through which the treatment mechanism is remotely operated by the operating unit. The operating unit has a cylindrical body provided with a first finger-retaining portion, and a slider slidably supported on the cylindrical body and provided with a second finger-retaining portion. The slider is connected to the connecting wire. By moving the slider relative to the cylindrical body using an operator's thumb retained on the first finger-retaining portion and the operator's index and middle fingers retained on the second finger-retaining portion, the connecting wire is moved by the same amount as the relative movement between the slider and the cylindrical body, to thereby operate the treatment mechanism.

Some endoscopic treatment tools require large movement of connecting wires in order to operate treatment mechanisms. For example, a front loop wire type treatment tool such as a high-frequency snaring tool and a basket type recovery tool are such types of tools. During the medical or surgical treatment using the endoscopic treatment tool of this type, the operator must spread his hand to increase a distance between his thumb and his index and middle fingers as much as possible as shown in FIG. 7, which hinders smooth operation of the tool.

In contrast, some other endoscopic treatment tools require fine movement of connecting wires to operate treatment mechanisms. For example, biopsy forceps having a pair of closable forceps pieces as the treatment mechanism requires fine movement of the connecting wire so that the forceps pieces properly nip and cut a diseased tissue.

SUMMARY OF THE INVENTION

An object of the present invention is to provide an operating unit for an endoscopic treatment tool, which is equipped with a motion converting mechanism that can convert a motion of fingers into a motion of a connecting wire in an amount appropriate for operating a treatment mechanism.

To achieve the above-noted object, the present invention provides an operating unit adapted for an endoscopic treatment tool. The endoscopic treatment tool has a medical or surgical treatment mechanism driven by movement of a connecting wire. The operating unit comprises a cylindrical body, a finger-retaining portion, a coupling member, and a motion converting mechanism. The finger-retaining portion is axially and movably arranged on the cylindrical body. The coupling member is axially and movably arranged on the cylindrical body, and is adapted to fixedly receive an end of the connecting wire thereon. The motion converting mechanism connects the finger-retaining portion to the coupling member, and converts axial movement of the finger-retaining portion into a different amount of axial movement of the coupling member.

The motion converting mechanism transmits the axial movement of the finger-retaining portion to the coupling member with a certain magnification, a certain reduction or a certain varying characteristic suitable for operating a treatment mechanism.

The present disclosure relates to the subject matter contained in Japanese patent application Nos. Hei. 9-221281 (filed on Aug. 18, 1997), Hei. 9-283056 (filed on Sep. 30, 1997), and Hei. 9-283057 (filed on Sep. 30, 1997), which are expressly incorporated herein by reference in their entireties.

BRIEF DESCRIPTION OF THE DRAWINGS

FIG. 1 is a side sectional view of an operating unit for an endoscopic treatment tool.

FIG. 2 is a side sectional view of the operating unit in a different state.

FIG. 3 is a side sectional view of another operating unit for an endoscopic treatment tool.

FIG. 4 is a side sectional view of the operating unit shown in FIG. 3 in a different state.

FIG. 5 is a side sectional view of another operating unit for an endoscopic treatment tool.

FIG. 6 is a side sectional view of the operating unit shown in FIG. 5 in a different state.

FIGS. 8A and 8B are side sectional views of another operating unit for an endoscopic treatment tool.

FIGS. 15A and 15B are sectional views of another operating unit for an endoscopic treatment tool.

FIG. 16 is a sectional view of the operating unit shown in FIGS. 15A and 15B.

FIG. 17 is a sectional view of the operating unit shown in FIGS. 15A and 15B in a different state.

DESCRIPTION OF THE OPERATING UNIT

Figure 7:
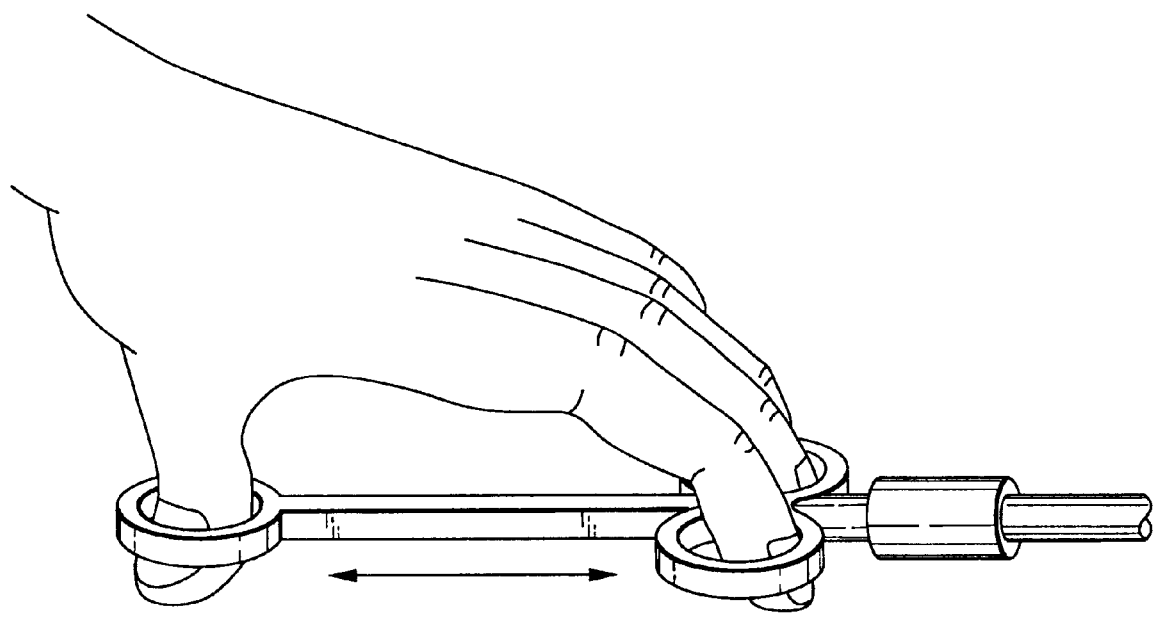
FIG. 7 is a perspective view showing a state in which a prior art operating unit for an endoscopic treatment tool is operated.

FIGS. 1 and 2 show an operating unit 4 for an endoscopic treatment tool. This operating unit 4 is characterized by a motion converting mechanism 36 (described in detail further below) that converts a motion of an operator's fingers into a motion of a connecting wire 604 with a certain magnification or amplification. Therefore, this operating unit 4 is preferably applied to various kinds of endoscopic treatment tools that require large motion of the connecting wire to operate medical or surgical treatment mechanisms.

As shown in FIG. 1, the basal end of a flexible sheath 602 is fixedly coupled to the tip end portion of a cylindrical body 8. The flexible sheath 602 is a tube made of, for example, polytetrafluoroethylene resin, and is adapted to be passed through a treatment tool insertion channel of an endoscope (not shown).

A flexible connecting wire 604 is passed through the sheath 602 so as to be received in the axial direction. The tip end of the connecting wire 604 is coupled to an elastic wire (not shown) which expands into a loop-like shape by its own elasticity when the elastic wire is protruded from the tip end of the sheath 602.

In the case of a high-frequency snaring tool, the elastic wire is designed to expand two-dimensionally into a planar form. In the case of a basket type recovery tool, the elastic wire is designed to expand three-dimensionally into a basket-like form. When the connecting wire 604 is pulled, the elastic wire is pulled and contracted into the tip end of the sheath 604 while being elastically deformed.

The connecting wire 604 is operatively moved relative to the sheath 602 while the operator's thumb is retained on a first finger-retaining portion 10 and the operator's index and middle fingers of the same hand are retained on second finger-retaining portions 1200. In this operating unit 4, the second finger-retaining portions 1200 are formed integrally with the cylindrical body 8.

The cylindrical body 8 is in the form of a relatively thick hollow cylinder. A first rack (stationary rack) 18 is formed on the inner peripheral face of the cylindrical body 8 so as to be formed in the axial direction from an opening on the side of the operator (in FIG. 1, the opening on the left-handed side) toward the opposite opening.

The basal end of the connecting wire 604 is fixed to a coupling member 14 by a manually operable fixing screw 28. The coupling member 14 is disposed inside the cylindrical body 8 so as to be disposed in the axial direction. When the fixing screw 28 is loosened, the connecting wire 604 can be detached from the coupling member 14 so as to be replaced with another connecting wire.

The fixing screw 28 is passed through an axially-elongated guide groove 32 of the cylindrical body 8, with the head of the fixing screw 28 protruding externally from the cylindrical body 8. The fixing screw 28 and the guide groove 32 cooperatively restrict the movement of the coupling member 14 within the cylindrical body 8 to be within a predetermined range.

A second rack (movable rack) 26 is formed on the coupling member 14 so as to face the first rack 18. The first and second racks 18 and 26 have identical pitch. A pinion 34, constructed by a single small gear, is arranged so as to mesh with both of the racks 18 and 26.

The pinion 34 is rotatably supported on a tip end of a connecting rod 19. The first finger-retaining portion 10 is integrally formed with the other end of the connecting rod 19, and the first finger-retaining portion 10 protrudes from the cylindrical body 8 toward the operator.

The motion converting mechanism 36 in this operating unit 4 includes the first rack 18, the second rack 26, the pinion 34 and the coupling member 14.

Operation of the thus configured operating unit 4 for an endoscopic treatment tool will now be described. The operator's fingers are respectively retained on the finger-retaining portions 10 and 1200, and the finger-retaining portions 10 and 1200 are then operatively moved to reduce a distance therebetween, thereby causing the connecting wire 604 to be moved in the forward direction, as shown in FIG. 2. Consequently, the elastic wire coupled to the tip end of the connecting wire 604 is pushed out from the end of the sheath 602. The abutment of the tip end face of the coupling member 14 against the cylindrical body 8 restricts further movement of the elastic wire.

During this operation, the pinion 34 meshing with both the first rack.18 of the cylindrical body 8 and the second rack 26 of the coupling member 14 results in the moving distance of the coupling member 14 relative to the cylindrical body 8 being twice as large as that of the connecting rod 19 relative to the cylindrical body 8. That is, the motion converting mechanism 36 converts a change in distance A between the first finger-retaining portion 10 and the second finger-retaining portions 1200 into a moving distance B of the connecting wire 604 relative to the sheath 602, where distance B is twice as large as distance A. Therefore, the operation stroke of the finger-retaining portion 10 can be half the movement stroke of the connecting wire 604.

Consequently, since the need to largely and forcibly increase the span between the fingers retained on the first and second finger-retaining portions 10 and 1200 can be eliminated, the operating unit 4 can be operated easily and smoothly using the fingers of a hand holding the operating unit 4. A fine movement operation of the connecting wire 604 is also facilitated.

FIGS. 3 and 4 show an operating unit 4 for an endoscopic treatment tool, which is a modification of the operating unit 4 shown in FIGS. 1 and 2. In this operating unit 4, the second finger-retaining portion 1200 is disposed on the coupling member 14 rather than on the cylindrical body 8, so as to be externally protruded through the elongated guide groove 32. Therefore, the range in which the second finger-retaining portion 1200 is movable in the guide groove 32 is equal to the movement stroke of the coupling member 14.

According to this modification, the connecting wire 604 and the second finger-retaining portion 1200 are moved together with the coupling member 14. Assuming that the cylindrical body 8 is stationary, the movement of the first finger-retaining portion 10 causes the movement of the coupling member 14 in the same direction to be twice as large as the movement of the first finger-retaining portion 10.

Therefore, a movement A of the first finger-retaining portion 10 is equal to half of the movement B of the connecting wire 604. In addition, a change in distance between the first finger-retaining portion 10 and the second finger-retaining portions 1200 (i.e., (the moving distance of the second finger-retaining portions 1200)—(the moving distance of the first finger-retaining portion 10)) can be reduced to half of the moving distance of the connecting wire 604 relative to the sheath 602. Consequently, this operating unit can attain the same effect as the operating unit shown in FIGS. 1 and 2.

FIGS. 5 and 6 show an operating unit 4 of an endoscopic treatment tool, which is another modification of the operating unit 4 shown in FIGS. 1 and 2. In the operating unit 4, the pinion 34 is in the form of a transmission gear comprised of a large gear 34a coaxially and integrally formed with a small gear 34b. The large gear 34a meshes with the first rack (movable rack) 26 formed on the coupling member 14, whereas the small gear 34*b* meshes with a second rack (movable rack) 18 formed on the connecting rod 19.

The pinion 34 is rotatably supported on the cylindrical body 8. The first finger-retaining portion 10 is formed on the connecting rod 19, and the second finger-retaining portion 1200 defined by a pair of flanges 1204 is formed on the cylindrical body 8. No rack is formed on the cylindrical body 8. The movement stroke of the coupling member 14 is restricted by both abutment between the coupling member 14 and the connecting rod 19, and abutment between the coupling member 14 and the cylindrical body 8.

According to this modification, the movement (moving distance A) of the first finger-retaining portion 10 relative to the second finger-retaining portions 1200 causes the movement (moving distance B) of the connecting wire 604 relative to the sheath 602 to be a certain amplification amount. This amplification amount depends on a gear ratio of the pinion 34, that is, the number of teeth of the large gear 34*a* to the number of teeth of the small gear 34*b*. Therefore, the amplification amount can be arbitrarily set by suitably selecting the numbers of teeth.

Figure 13:
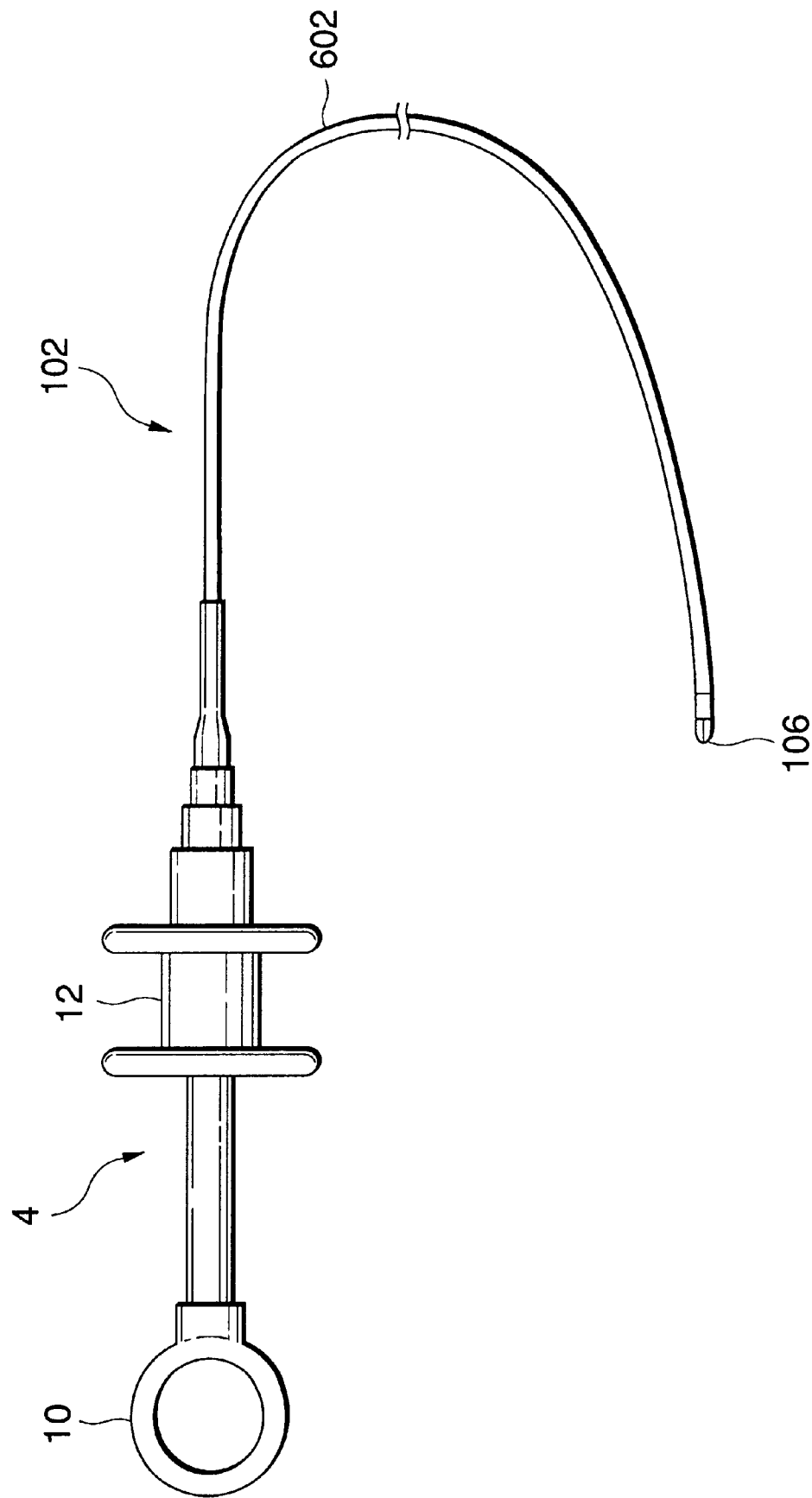
FIG. 13 is a schematic view of biopsy forceps to which the operating unit shown in FIGS. 8A and 8B is applied.

FIGS. 8A and 8B show another operating unit 4 for an endoscopic treatment tool. This operating unit 4 is characterized by a motion converting mechanism 36 which converts the motion of operator's fingers into the motion of a connecting wire 604, reduced by a certain amount. Accordingly, this operating unit is preferably applied to various kinds of endoscopic treatment tools that require fine or delicate motion of the connecting wires in order to operate medical or surgical treatment mechanisms. FIG. 13 schematically shows an example in which this operating unit 4 is applied to biopsy forceps 102 having a pair of closable forceps pieces 106 as a treatment mechanism. The tip end of the connecting wire 602 is connected to the forceps pieces 106 to operatively open and close the forceps pieces 106 using the operating unit 4.

The operating unit 4 includes a cylindrical member 8 elongated over a predetermined length, a ring-like first finger-retaining portion 10 rotatably fixed to the longitudinal basal end of the cylindrical member 8, and a slider 12 slidably supported on the cylindrical member 8.

The connecting wire 604 is passed through a flexible sheath 602 made of a closely wound coil. A coupling member 14 is attached to the tip end of the connecting wire 604.

A longitudinally-elongated groove 16 is formed in the cylindrical member 8. The groove 16 is rectangular in section as shown, for instance, in FIG. 9, and is externally opened. A first rack 18 is formed on the bottom of the groove 16 to extend along the groove 16 in the elongating direction.

The slider 12 has a pair of flanges 1204 longitudinally spaced from each other to form a second finger-retaining portion 1200. The slider 12 is formed with a central hole 22 through which the slider 12 is slidably mounted on the cylindrical body 8.

Figure 9:
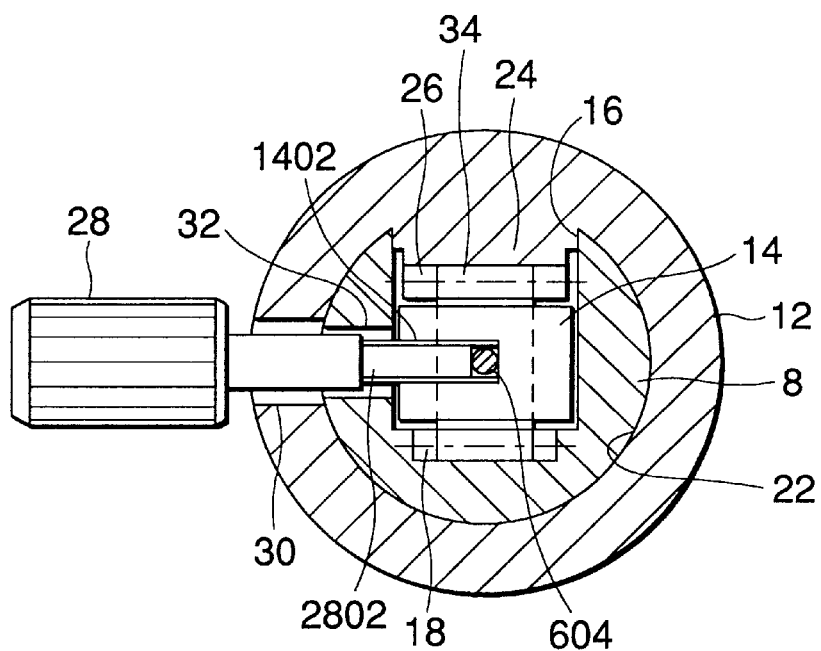
FIG. 9 is a sectional view taken along line 9—9 of FIG. 8B.
Figure 10:
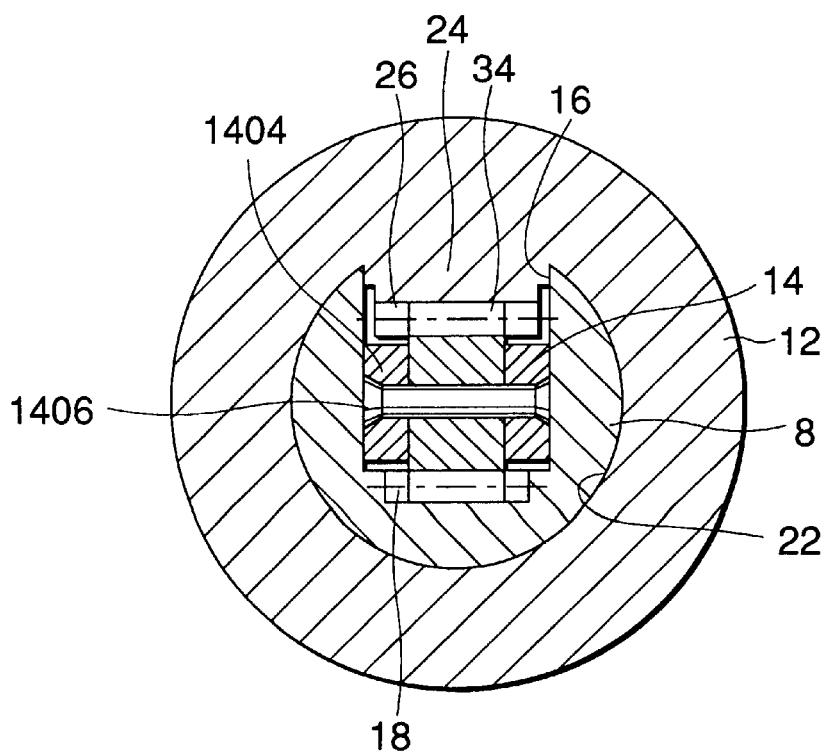
FIG. 10 is a sectional view taken along line 10—10 of FIG. 8B.
Figure 11:
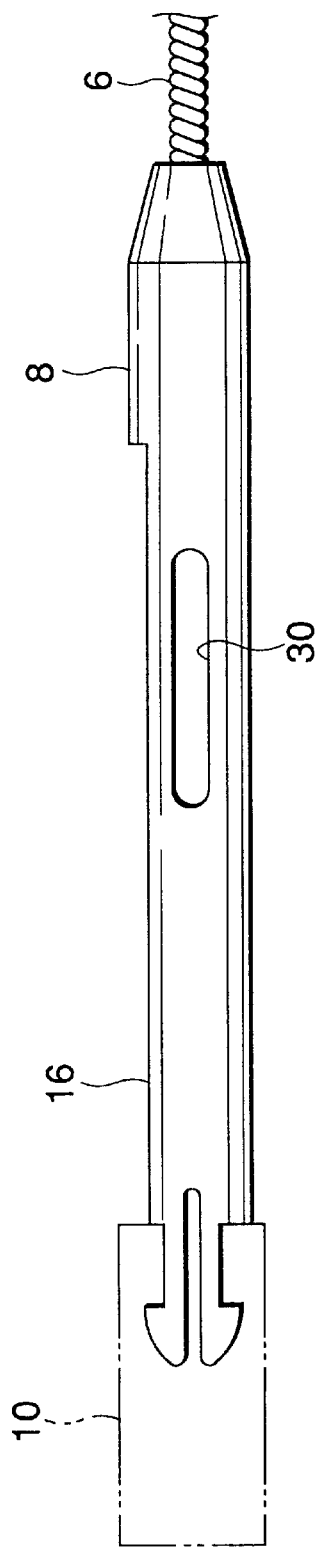
FIG. 11 is a plane view of a cylindrical member in the operating unit shown in FIGS. 8A and 8B.

As shown in FIGS. 9 and 10, the slider 12 is provided with a protrusion 24 having a rectangular sectional shape, which is radially, inwardly protruded from the inner peripheral face of the center hole 22 and elongated along the entire longitudinal length of the slider 12. A second rack 26 is formed on the protruded end face of the protrusion 24 entirely along the longitudinal length thereof. The second rack 26 faces toward and extends in parallel to the first rack 18.

The protrusion 24 is inserted into the groove 16, so that the slider 12 is slidable along the longitudinal direction of the cylindrical member 8, and is prevented from rotating with respect to the cylindrical member 8.

The coupling member 14 has a width corresponding to a width of the groove 16, and a height smaller than a gap between the first and second racks 18 and 26. The coupling member 14 is disposed inside the groove 16 so as to be movable along the groove 16.

As shown in FIG. 9, the end of the connecting wire 604 is attached to the coupling member 14 by a fixing screw (i.e., a male thread) 28. The fixing screw 28 is passed through an elongated opening 30 of the slider 12 and an elongated opening 32 of the cylindrical member 8 so that a male thread portion 2802 is threadingly engaged with a female thread 1402 of the coupling member 14. The fixing screw 28 is slidingly moved along the elongated openings 30 and 32, together with the connecting wire 604 and the coupling member 14.

Figure 12:
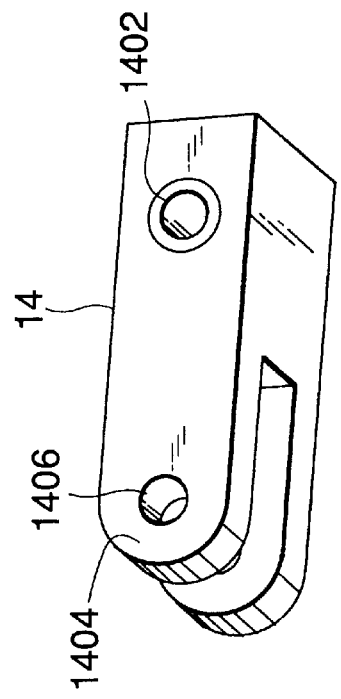
FIG. 12 is a perspective view of a coupling member in the operating unit shown in FIGS. 8A and 8B.

As shown in FIGS. 10 and 12, the end portion of the coupling member 14 is formed into a forked portion 1404 that rotatably supports a pinion 34 via a shaft 1406. The pinion 34 always meshes with both the first and second racks 18 and 26.

The motion converting mechanism 36 includes the first rack 18, the second rack 26, the pinion 34, and the coupling member 14. The motion converting mechanism 36 converts the movement of the slider 12 relative to the cylindrical body 8 into movement of the connecting wire 604 relative to the sheath 602, with a certain reduction in distance. With the aid of the converting mechanism 36, the movement of the slider 12 causes the connecting wire 604 to be moved in the same direction as the moving direction of the slider 12, and for a moving distance that is smaller than a moving distance of the slider 12.

In this operating unit 4, the pinion 34 meshes, at its diametrically opposite sides, with the first rack 18 that is stationary, and the second rack 26 which is moved together with the slider 12. When the thumb is retained on the finger-retaining portion 10, the index and middle fingers are held between flanges 1204, and the slider 12 is slidingly moved with respect to the cylindrical member 8, as shown in FIGS. 8A and 8B. The pinion 34 follows the movement of the slider 12 while rotating, in the same direction as the slider 12, and by a moving distance that is one half that of the slider 12.

Consequently, the connecting wire 604 coupled to the pinion 34 via the coupling member 14 follows the movement of the slider 12 to be moved in the same direction as the slider 12 and by a moving distance that is one half that of the slider 12.

Therefore, when this operating unit 4 is applied to biopsy forceps as shown in FIG. 13, a pair of forceps pieces 106 are operatively opened and closed by moving the slider 12 two strokes. As a result, the opening state of the pair of forceps pieces 106 can be finely adjusted.

Figure 14A:
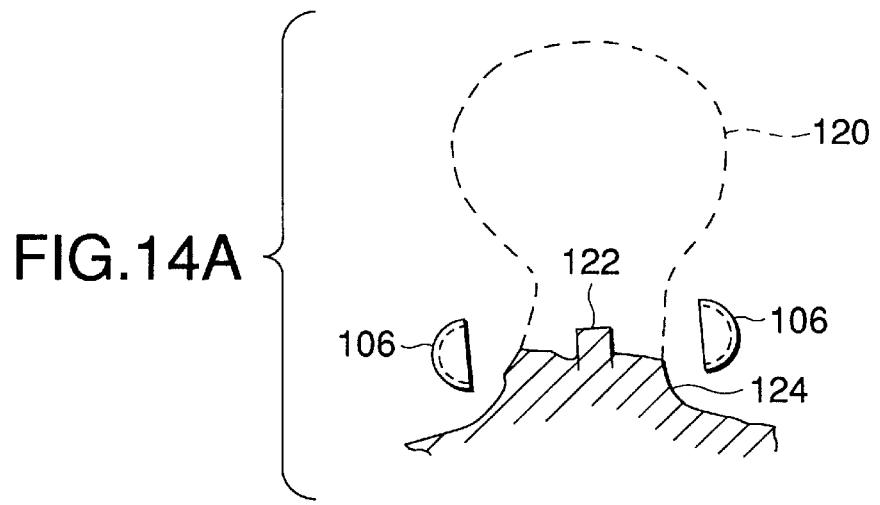
FIGS. 14A, 14B, and 14C are diagrams showing an operation of nipping a thin blood vessel using a pair of forceps pieces.

This operating unit 4 may also be applied to hot biopsy forceps. Hot biopsy forceps are used for cauterization, coagulation, and arrest of bleeding by nipping a thin blood vessel 122 with a pair of forceps pieces 106 and by applying high-frequency current to the forceps pieces 106 if the thin blood vessel 122 projects from an amputated stump formed as a result of a surgical-operation of cutting away a polyp 120 and bleeding occurs from the blood vessel 122. The pair of forceps pieces 106 can be slowly closed (from a state in which the forceps pieces 106 are almost completely closed), and the blood vessel 122 can be easily nipped using the forceps pieces 106 without erroneously nipping a stem 124 of the polyp 120, as shown in FIGS. 14A and 14C.

Figure 14B:
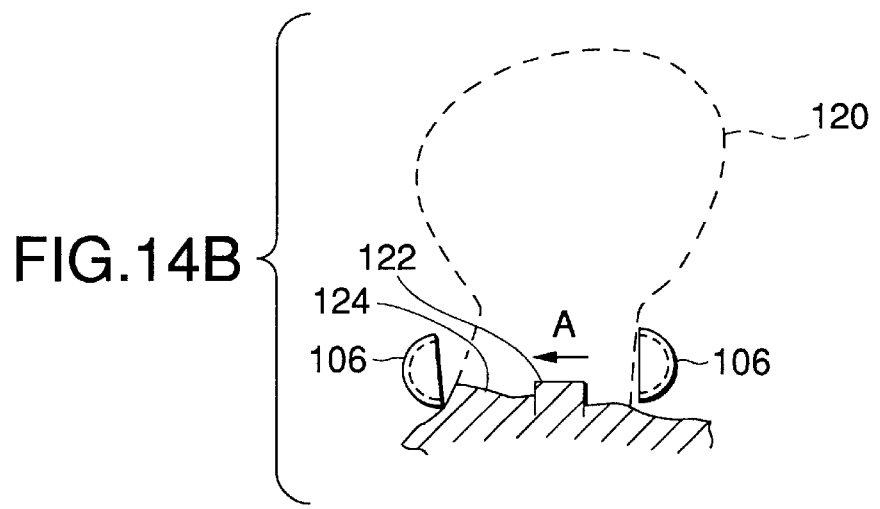
Figure 14C:
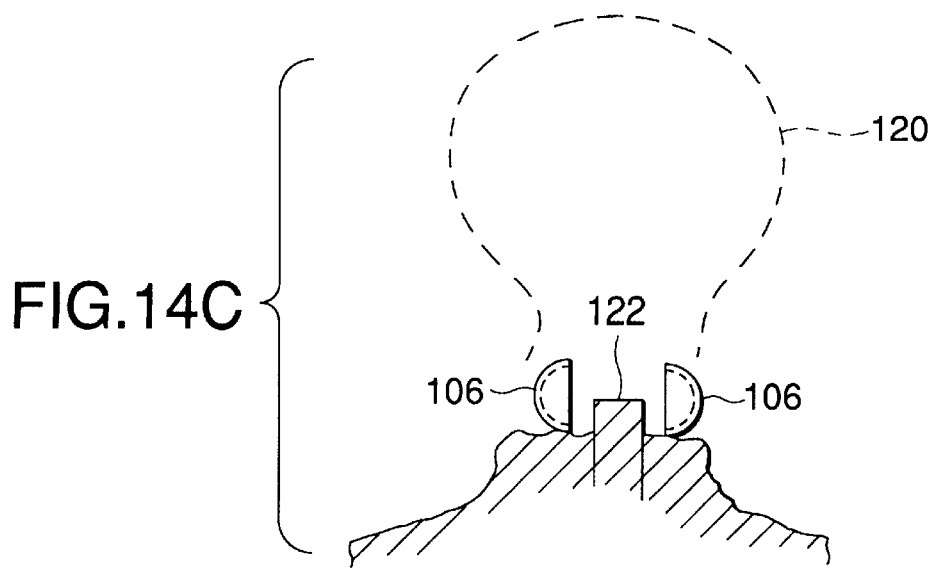

Even if one of the forceps pieces 106 is engaged with the stem 124 as shown in FIG. 14B, the pair of forceps pieces 106 can be slowly closed (from a state in which the forceps pieces are almost completely closed), so that the blood vessel 122 can be easily nipped without an erroneous operation in which the forceps pieces 106 are closed while the other forceps piece passes over the blood vessel 122, as indicated by arrow A in FIG. 14B. That is to say, with the operating unit 4, the opening state of the pair of forceps pieces 106 can be finely adjusted.

Similarly to the operating unit 4 shown in FIGS. 5 and 6, the operating unit 4 shown in FIGS. 8A and 8B may be modified such that a second pinion different in diameter from the pinion 34 is disposed coaxially with the pinion 34. The second pinion may be rotated together with the pinion 34, and one of the pinion 34 and the second pinion meshes with the first rack 18, whereas the other pinion meshes with the second rack 26. According to this modification, the movement distance of the connecting wire 604 with respect to the movement of the slider 12 can be changed to a desired value.

FIGS. 15A and 15B show another operating unit 4 for an endoscopic treatment tool. This operating unit 4 is characterized by a motion converting mechanism 36 which converts the motion of an operator's fingers into a motion of a connecting wire 604 with a certain variation in distance.

The motion converting mechanism 36 includes a link mechanism through which the slider 12 and the coupling member 14 are coupled to each other. The connecting wire 604 is connected to the coupling member 14.

Figure 19:
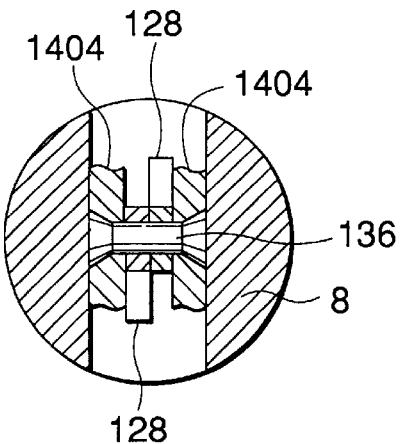
FIG. 19 is a sectional view taken along the line 19—19 of FIG. 15A.

As shown in FIGS. 16 and 19, the coupling member 14 has a forked portion 1404 that rotatably supports second links 128.

Figure 20:
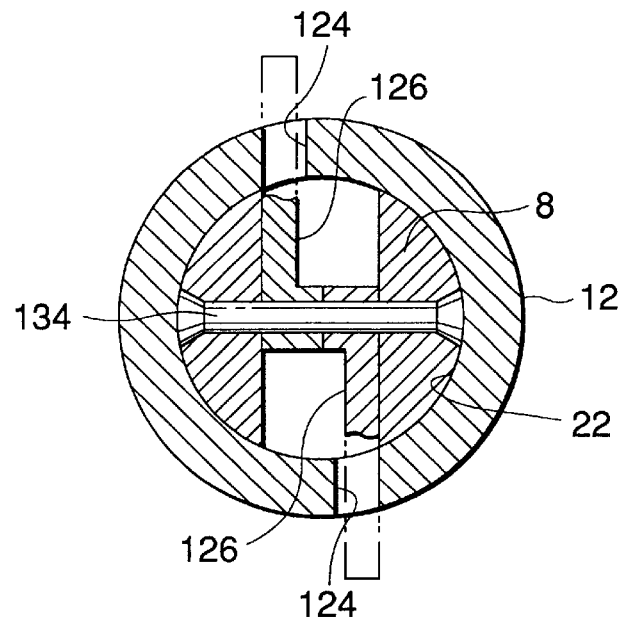
FIG. 20 is a sectional view taken along the line 20—20 of FIG. 15A.
Figure 21:
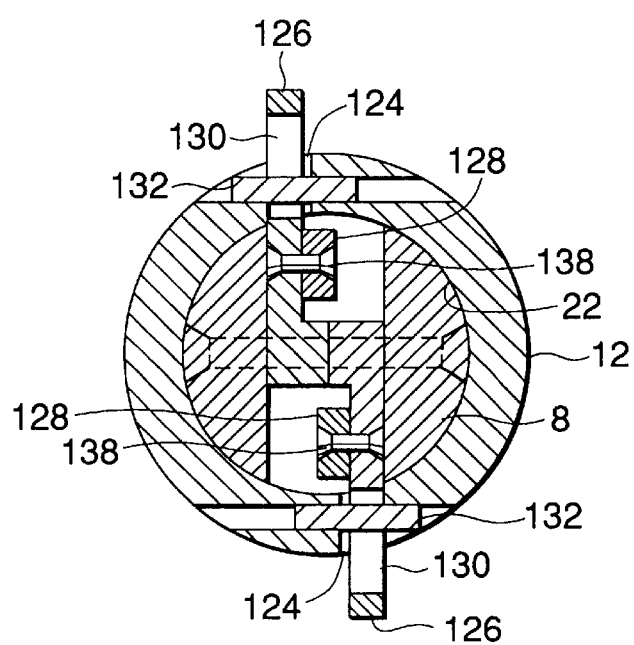
FIG. 21 is a sectional view, which is a combination of sectional views respectively taken along the lines 21—21 and 21'—21' of FIG. 15A.

As shown in FIGS. 16, 20, and 21, elongated grooves or slits 124 are formed in the tip end portion of a cylindrical portion 1202 of the slider 12 and located at diametrically opposite sides of the cylindrical portion 1202. Each of the elongated grooves 124 is open toward the tip end direction.

The link mechanism 13 disposed in the elongated groove 16 is constructed of two first links 126 and two second links 128. The link mechanism 13 may alternatively be constructed by a single first link 126 and a single second link 128.

A slot 130 is formed in each of the first links 126 at a location closer to one longitudinal end of the first link 126. As shown in FIGS. 16 and 21, the one longitudinal end of each first link 126 is placed in the corresponding elongated groove 124, and is slidably supported via the corresponding slot 130 and shaft 132 to the slider 12. As shown in FIGS. 16 and 20, the other longitudinal ends of the first links 126 are rotatably coupled to the cylindrical member 8 via a shaft 134.

As shown in FIGS. 16 and 19, one of the longitudinal ends of each of the second links 128 is rotatably coupled to the forked portion 1404 of the coupling member 14 via a shaft 136. As shown in FIGS. 16 and 21, the other of each of the longitudinal ends of the second links 128 are rotatably coupled to intermediate portions of the first links 126 via shafts 138.

When the slider 12 is moved on and along the cylindrical member 8, the coupling member 14 is moved via the link mechanism 13 in the same direction as the slider 12, and the wire 604 is accordingly moved together with the coupling member 14.

Operation of the operating unit 4 will now be described with reference to a case where the operating unit 4 is applied to a hot biopsy forceps.

Figure 18:
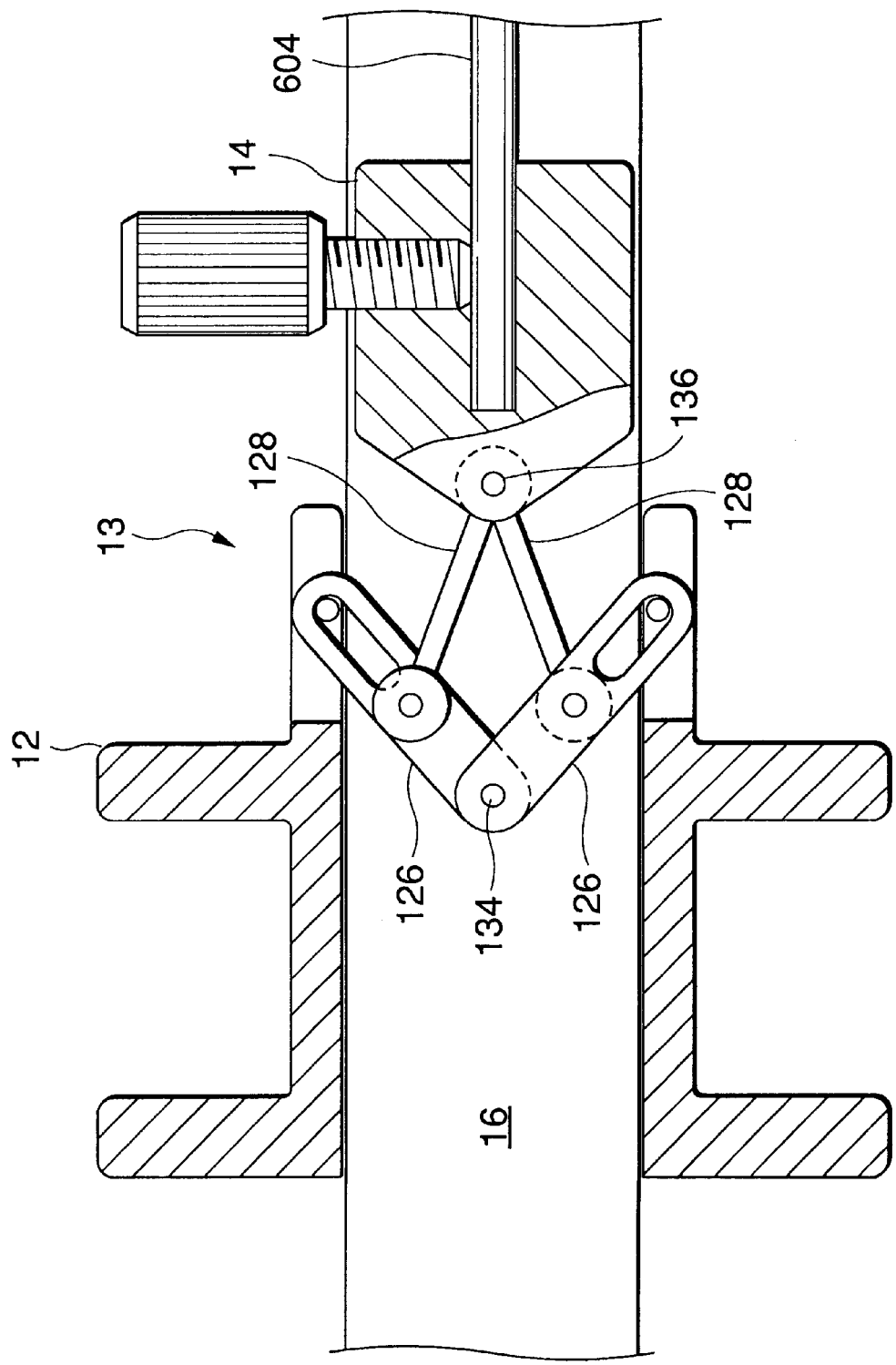
FIG. 18 is a sectional view of the operating unit shown in FIGS. 15A and 15B in another state.

In the state shown in FIGS. 15A and 16 (i.e., the state in which the slider 12 is positioned on the side of the basal end of the cylindrical member 8), the pair of forceps pieces of the hot biopsy forceps are fully closed. With operator's thumb retained on the first finger-retaining portion 10 and operator's index and middle fingers retained on the second finger-retaining portion 1200 defined by the flanges 1204, the slider 12 is slidingly moved toward the tip end side relative to the cylindrical member 8 as shown in FIG. 17. The first links 126 are moved so as to become erect using the shaft 134 as the fulcrum. The second links 128 follow the movement of the shafts 138 to increase an inner angle between the second links 128 about the shaft 138, whereby the coupling member 14 and the wire 604 are forwardly pushed and the pair of forceps pieces are gradually opened from the fully closed state. When the slider 12 is moved further toward the tip end side of the cylindrical member 8 to establish the state shown in FIGS. 15B and 18, the pair of forceps pieces 106 are fully opened.

The movement of the wire 604 per unit stroke of the slider 12 can be set to have a desired value or a desired characteristic. This setting is accomplished by adequately selecting the lengths of the first and second links 126 and 128, and the positions of the shafts 138 in the first links 126.

Figure 22:
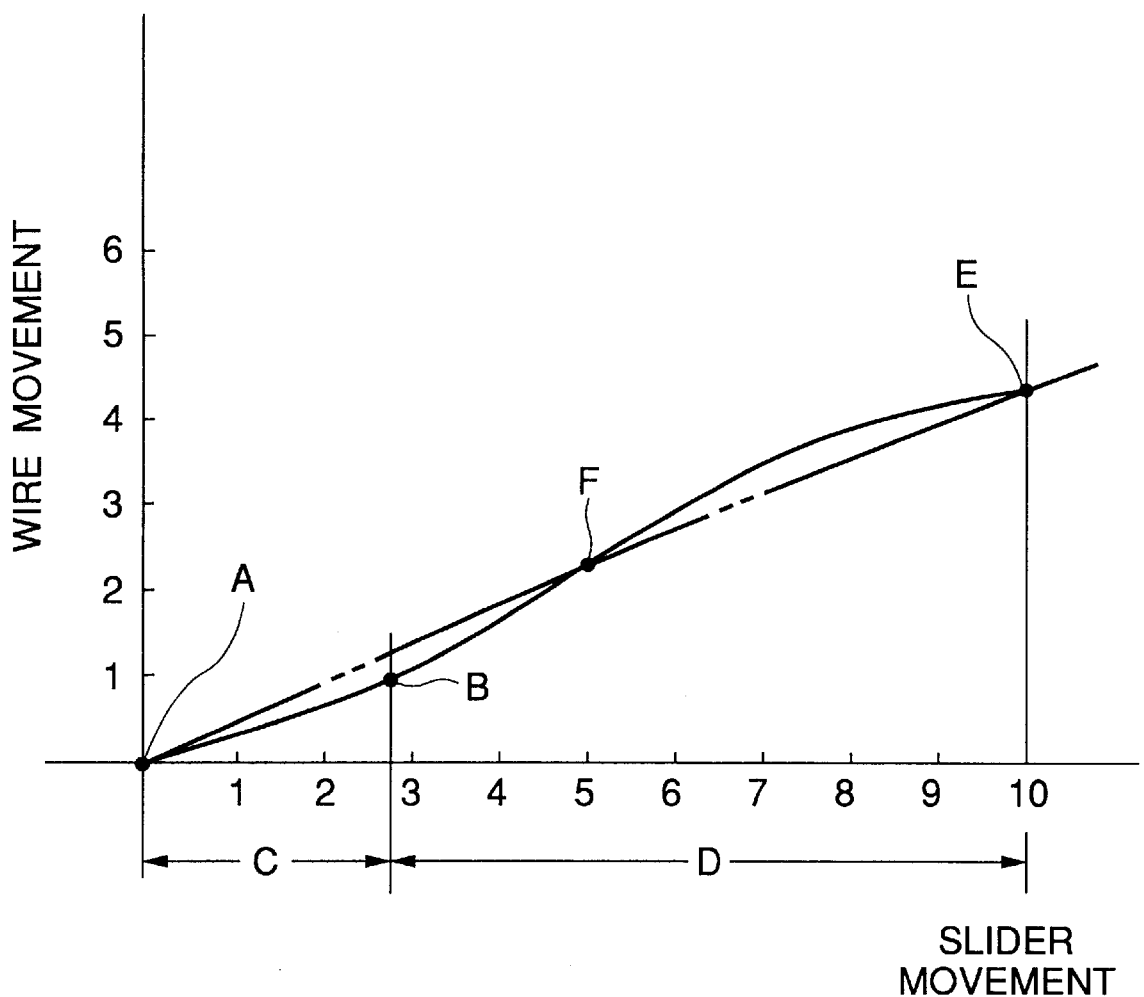
FIG. 22 is a graph showing relationships between the moving distance of a slider and that of a connecting wire.

FIG. 22 shows a characteristic of the connecting wire 604 movement in conjunction with the movement of the slider 12. In FIG. 22, reference character C designates a moving range or moving distance of the slider 12 from a state A where the forceps pieces are fully closed to a state B where the forceps pieces are slightly open. Reference character D designates a moving-range or moving distance of the slider 12 from the state B to a state E where the forceps pieces are fully open. The ratios of the connecting wire 604 movement relative to the slider 12 movement in the moving region C is set to be smaller than the ratios of the connecting wire movement relative to the slider movement in the moving region D. When the moving range of the slider 12 from the fully closed state A to the fully opened state E is considered to be one stroke, the range C is set to be substantially one fourth of the entire stroke, whereas the range D is set to be substantially three fourths thereof. Further, during the entire range (i.e., the entire stroke) of the slider 12 from lo the fully opened state A to the fully closed state E, the moving distance of the connecting wire 604 is smaller than the moving distance of the slider 12.

Since the connecting wire 604 in the vicinity of the fully closed state has a small moving distance per unit stroke of the slider 12, the opening state of the forceps pieces can be finely adjusted in the vicinity of the fully closed state.

Therefore, the pair of forceps pieces can be slowly closed from a state in which the forceps pieces are almost completely closed, and the blood vessel can easily be nipped by the forceps pieces without erroneously nipping a stem of a polyp.

Even if one of the forceps pieces is engaged with the stem, the pair of forceps pieces can be slowly closed from a state in which the forceps pieces are almost completely closed. Thus, so that the blood vessel can easily be nipped without an erroneous operation in which the forceps pieces are closed while one of the forceps pieces passes over the blood vessel.

The movement of the connecting wire 604 per unit stroke of the slider 12 can be set to have a desired value or a desired characteristic by adequately selecting the lengths of the first and second links 126 and 128, and the positions of the shafts 138 in the first links 126. This is accomplished by changing the configuration of the link mechanism 13 itself, or by configuring the motion converting mechanism 36 using a gear mechanism or the like.

For example, as shown in FIG. 22, assuming that a first range is defined between the fully closed state A and an intermediate state F in which the forceps pieces are half-opened, whereas a second range is defined between the intermediate state F and the fully opened state E, the moving distance of the connecting wire 604 per unit stroke of the slider 12 in the first range may be set to be smaller than that in the second range.

In this setting also, the opening state of the forceps pieces can be finely adjusted in the vicinity of the fully closed state. Therefore, the thin blood vessel or the like can easily and surely be nipped, and various treatments can be easily performed.

What is claimed is:

1. An operating unit adapted for an endoscopic treatment tool, said endoscopic treatment tool having a medical or surgical treatment mechanism driven by movement of a connecting wire, said operating unit comprising:
    a cylindrical body;
    a finger-retaining portion axially movably arranged on said cylindrical body;
    a coupling member arranged axially movably on said cylindrical body, said coupling member adapted to fixedly receive an end of said connecting wire thereon; and
    a motion converting mechanism connecting said finger-retaining portion to said coupling member, wherein said motion converting mechanism converts axial movement of said finger-retaining portion into a different amount of axial movement of said coupling member with a certain magnification; and
    wherein said motion converting mechanism includes:
        a first rack formed on said cylindrical body;
        a second rack formed on said coupling member; and
        a pinion rotatably supported on said finger-retaining portion, said pinion meshing with both said first and second racks.

2. An operating unit according to claim 1, further comprising:
    a second finger-retaining portion formed on said cylindrical body.

3. An operating unit according to claim 1, further comprising:
    a second finger-retaining portion formed on said coupling member.

4. An operating unit adapted for an endoscopic treatment tool, said endoscopic treatment tool having a medical or surgical treatment mechanism driven by movement of a connecting wire, said operating unit comprising:
    a cylindrical body;
    a finger-retaining portion axially movably arranged on said cylindrical body;
    a coupling member arranged axially movably on said cylindrical body, said coupling member adapted to fixedly receive an end of said connecting wire thereon; and
    a motion converting mechanism connecting said finger-retaining portion to said coupling member, wherein said motion converting mechanism converts axial movement of said finger-retaining portion into a different amount of axial movement of said coupling member with a certain magnification; and
    wherein said motion converting mechanism includes:
        a first rack formed on said finger-retaining portion;
        a second rack formed on said coupling member; and
        a pinion rotatably supported on said cylindrical body, said pinion having small and large gears connected integrally and coaxially to each other, said small and large gears meshing with said first and second racks, respectively.

5. An operating unit according to claim 1, further comprising:
    second finger-retaining portion formed on said cylindrical body.

6. An operating unit adapted for an endoscopic treatment tool, said endoscopic treatment tool having a medical or surgical treatment mechanism driven by movement of a connecting wire, said operating unit comprising:
    a cylindrical body;
    a finger-retaining portion axially movably arranged on said cylindrical body;
    a coupling member arranged axially movably on said cylindrical body, said coupling member adapted to fixedly receive an end of said connecting wire thereon; and
    a motion converting mechanism connecting said finger-retaining portion to said coupling member, wherein said motion converting mechanism converts axial movement of said finger-retaining portion into a different amount of axial movement of said coupling member; and
    wherein said motion converting mechanism transmits the axial movement of said finger-retaining portion to said coupling member with a certain reduction.

7. An operating unit according to claim 6, wherein said certain reduction is defined by a ratio of axial movement of said coupling member relative to axial movement of said finger-retaining portion causing said axial movement of said coupling member, and said ratio is 1/2.

8. An operating unit according to claim 6, wherein said motion converting mechanism includes:
    a first rack formed on said cylindrical body;
    a second rack formed on said finger-retaining portion; and
    a pinion rotatably supported on said coupling member, said pinion meshing with both said first and second racks.

9. An operating unit according to claim 6, wherein said finger-retaining portion includes a slider axially movably arranged on said cylindrical body.

10. An operating unit according to claim 6, further comprising:
    a second finger-retaining portion provided on said cylindrical body.

11. An operating unit adapted for an endoscopic treatment tool, said endoscopic treatment tool having a medical or surgical treatment mechanism driven by movement of a connecting wire, said operating unit comprising:
    a cylindrical body;
    a finger-retaining portion axially movably arranged on said cylindrical body;
    a coupling member arranged axially movably on said cylindrical body, said coupling member adapted to fixedly receive an end of said connecting wire thereon; and
    a motion converting mechanism connecting said finger-retaining portion to said coupling member, wherein said motion converting mechanism converts axial movement of said finger-retaining portion into a different amount of axial movement of said coupling member with a certain varying characteristic; and wherein said varying characteristic is defined by a ratio of axial movement of said coupling member relative to axial movement of said finger-retaining portion causing said axial movement of said coupling member, and said ratio gradually increases and thereafter gradually decreases as said finger-retaining portion is moved toward said coupling member.

12. An operating unit according to claim 11, wherein said motion converting mechanism includes:

a plurality of links cooperatively connecting said finger-retaining portion to said coupling member.

13. An operating unit according to claim 11, wherein said motion converting mechanism includes:

a first link connecting said finger-retaining portion to said cylindrical body;

a second link connecting said first link to said coupling member.

14. An operating unit according to claim 13, wherein one end of said first link is rotatably supported by said cylindrical body, the other end of said first link is rotatably and slidably supported by said finger-retaining portion, one end of said second link is rotatably supported by said first link and the other end of said second link is rotatably supported by said coupling member.

15. An operating unit according to claim 11, further comprising:

a second finger-retaining portion provided to said cylindrical body.

* * * * *